United States Patent [19]

Botchan et al.

[11] Patent Number: 5,620,849
[45] Date of Patent: *Apr. 15, 1997

[54] METHODS AND COMPOSITIONS FOR IDENTIFYING INHIBITORS OF PAPILLOMA VIRUS REPLICATION

[75] Inventors: Michael R. Botchan, Kensington; Liu Yang, Berkeley; Rong Li, El Cerrito; Ian J. Mohr, Berkeley; Robin Clark, Oakland, all of Calif.

[73] Assignees: Cetus Corporation, Emeryville, Calif.; The Regents of the University of California, Oakland, Calif.

[*] Notice: The portion of the term of this patent subsequent to Dec. 21, 2010, has been disclaimed.

[21] Appl. No.: 311,406

[22] Filed: Sep. 23, 1994

Related U.S. Application Data

[63] Continuation of Ser. No. 124,567, Sep. 20, 1993, abandoned, which is a continuation of Ser. No. 775,273, Oct. 11, 1991, abandoned.

[51] Int. Cl.$^6$ .............................. C12Q 1/68; C12N 7/00; A61K 38/43; C07K 2/00
[52] U.S. Cl. .......................... 435/6; 435/235.1; 435/239; 424/94.1; 424/94.2; 536/23.72; 530/300
[58] Field of Search .............................. 435/5, 6, 235.1, 435/239; 530/350, 300; 536/23.72; 424/94.1, 94.2

[56] References Cited

FOREIGN PATENT DOCUMENTS 0257754  3/1988  European Pat. Off. .
0302758  2/1989  European Pat. Off. .

OTHER PUBLICATIONS

Ira L. Blitz et al., "The 68–Kilodalton E1 Protein of Bovine Papillomavirus Is a DNA Binding Phosphoprotein Which Associates with the E2 Transcriptional Activator in Vitro", *J. of Virol.* (1991) 65(2):649–656.

Cheng–Ming Chiang et al., "An E1M E2C Fusion Protein Encoded by Human Papillomavirus Type 11 is a Sequence–Specific Transcription Repressor", *J. of Virol.* (1991) 65(6):3317–3329.

Jonathan D. Knight et al., "The activation domain of the bovine papillomavirous E2 protein mediates association of DNA–bound dimers to form DNA loops", *Proc. Natl. Sci. USA* (1991) 88:3204–3208.

Rong Li et al., "Direct Interaction between Sp1 and the BPV Enhancer E2 Protein Mediates Synergistic Activation of Transcription" *Cell* (1991) 65:493–505.

Joachim J. Li et al., "Simian virus 40 DNA replication *in vitro*" *Proc. Natl. Acad. Sci. USA* (1984) 81:6973–6977.

Ian J. Mohr et al., "Targeting the E1 Replication Protein to the Papillomavirus Origin of Replication by Complex Formation with the E2 Transactivator" *Science* (1990) 250:1694–1699.

Hiromasa Sekine et al., "Expression of human papillomavirus type 6b E2 gene product with DNA–binding activity in insect (*Bombyx mori*) cells using a baculovirus expression vector" *Gene* (1988) 65:187–193.

Liu Yang et al., "Activation of BPV–1 replication *in vitro* by the transcription factor E2" *Nature* (1991) 353:628–632.

Gangemi et al. 1994 Antiviral Res. 24:175–190.

Chalberg 1989 Annu rev. Biochem 58:671–717.

Gilbert et al. 1987, Cell. 50:59–68.

Ustav & Stenland. 1991 EMBO J. 10(2):449.

Li & Kelly 1984. PNAS. 81:6973.

Primary Examiner—Robert A. Wax
Assistant Examiner—K. Cochrane Carlson
Attorney, Agent, or Firm—Reed & Robins

[57] ABSTRACT

Compositions and methods for identifying inhibitors of papilloma virus replication are described consisting of soluble cellular extracts supplemented with purified viral E1 and E2 proteins.

7 Claims, 7 Drawing Sheets

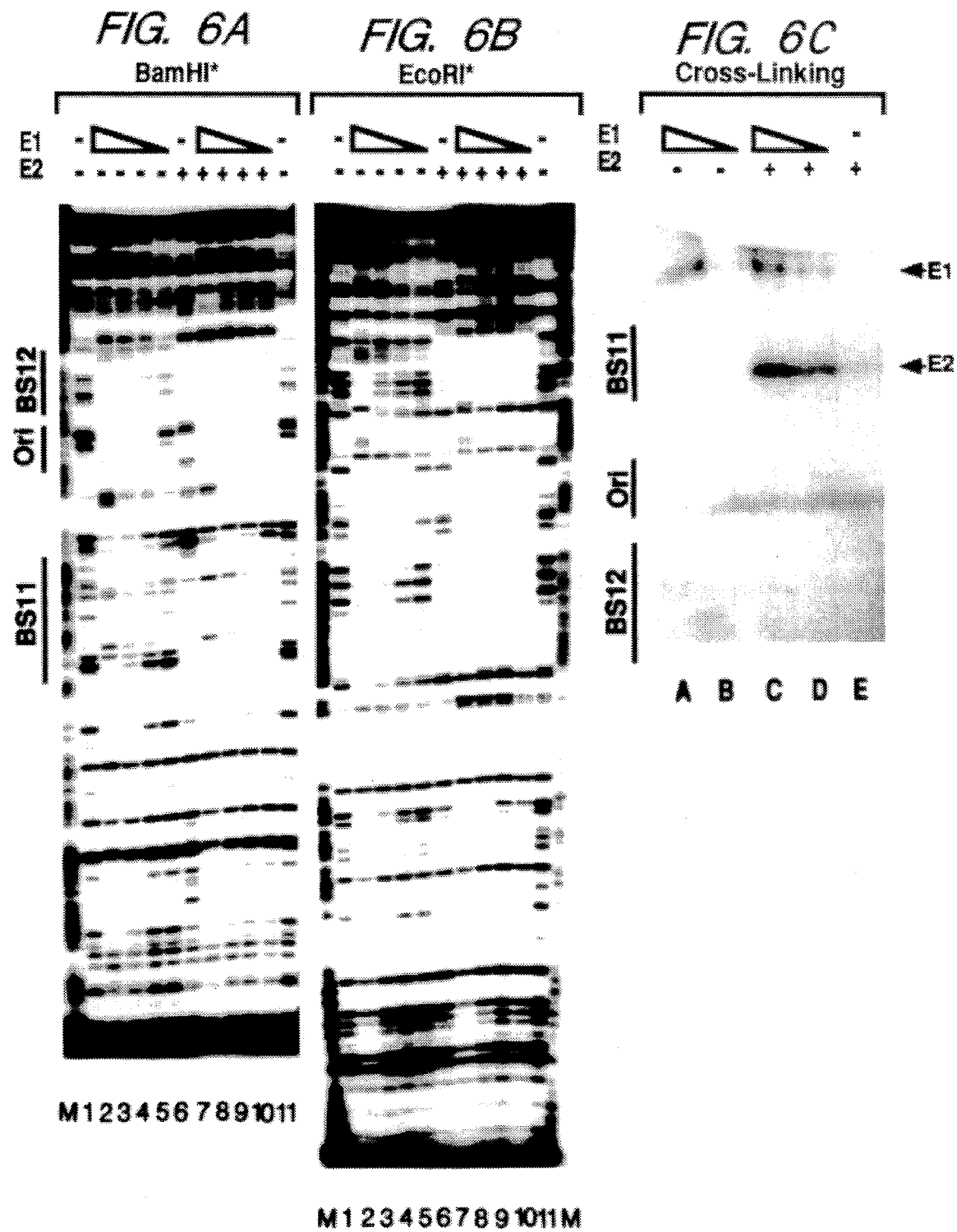

— 5,620,849 —

METHODS AND COMPOSITIONS FOR IDENTIFYING INHIBITORS OF PAPILLOMA VIRUS REPLICATION

This application is a continuation of application Ser. No. 08/124,567 filed on 20 Sept. 1993, now abandoned, which is a continuation of 07/775,273, filed 11 Oct. 1991, now abandoned.

FIELD OF THE INVENTION

This invention is in the field of molecular biology with emphasis on the identification of medicaments that can be used to treat papilloma virus diseases, particularly warts and cancers.

BACKGROUND OF THE INVENTION

Different pathways are likely to regulate the initiation of DNA replication. For example, the post-translational modification of the proteins required for synthesis are known to be pivotal in intricate ways[1–5]. Interestingly, proteins that bind to origins of replication also function in the control of transcription[6,7]. The roles of transcription factors in regulating chromosomal replication are ambiguous. However, numerous experiments have shown that tissue-specific gene expression is correlated with early replication of the active gene and its flanking DNA, while the same gene when inactive in another tissue replicates late in the cell cycle[8]. This implies a link between transcription control and replication control.

Bovine Papilloma Virus type 1 (BPV-1) provides a framework for exploring the roles of transcription factors in eukaryotic DNA replication. In transformed cells, the viral chromosome is maintained as a stable nuclear plasmid replicating in synchrony with the host DNA. Two vital proteins, E1 and E2, are both necessary and sufficient for replication[9]. E1 is a 68 kD protein and vital DNA with mutations in this ATP binding protein cannot be maintained as nuclear plasmids[10]. Three related site-specific DNA binding proteins are encoded by the E2 ORF[1]: a 48 kD transactivator and two repressor lacking the activation domain, E2C and E8/E2. The 48 kD transactivator binds to DNA as a dimer, and in combination with cellular factors including SP-1[12] activates transcription from a number of vital promoters. The relative concentrations of the E2 family of ;proteins thus intricately regulate the transcriptional program of the viral plasmids. Studies from our laboratory showed that the 48 kD E2 protein could form a tight complex with the E1 protein[13]. Partially purified E1 displayed a weak specific DNA binding activity, and this activity was markedly stimulated by E2. To facilitate mechanistic studies and to ascertain if E2 plays a direct role in DNA replication, we developed a cell-free replication system.

SUMMARY OF THE INVENTION

A first object of the invention is a description of a method of identifying compounds that inhibit papilloma virus DNA replication, consisting of isolating a cell free extract that supports papilloma virus DNA replication in the presence of papilloma virus proteins E1 and E2; forming a mixture consisting of the cell flee extract, E1 and E2, assay reagents that support and permit the determination of papilloma virus DNA replication, and the compounds; and measuring the amount of DNA replication that occurs in the presence of said compounds compared to the amount that occurs in their absence.

A second object of the invention is a description of a composition for replicating papilloma virus DNA, comprising papilloma virus proteins E1 and E2, and a cell free extract that supports papilloma virus DNA replication.

These and other objects of the invention will become apparent upon a full consideration of the following disclosure.

BRIEF DESCRIPTION OF THE DRAWINGS

FIGS. 6A–C, A and B, Binding of E1 to the origin of BPV replication is stimulated by E2. DNA fragments containing BPV sequence 7805-100 were labeled with $^{32}$P at 5'-end of each strand (A, top strand with labeling at Bam HI site; B, bottom strand with labeling at Eco RI site). The DNase I footprint analysis was performed as described before[12] with following modifications. The Z buffer was replaced with a new buffer containing 20 mM potassium phosphate (pH7.5), 100 mM potassium glutamate, 1 mM EDTA, 0.5 mM DTT and 10% Glycerol. The binding reaction was carried out at 37° C. for 15 min, followed by standard DNase I digestion. E1 concentration: lanes 2 and 7, 900 ng; lanes 3 and 8, 300 ng; lanes 4 and 9, 100 ng; lanes 5 and 10, 33 ng. E2concentration:lanes 6–10, 100 ng. BS11 and BS12, E2 binding sites 11 and 12. M, AG sequence size marker. C, E1 is required for the interaction of E2 with DNA in the absence of E2 binging sites. The interaction of E1 and E2 with DNA were probed by UV-crosslinking of the proteins to a [$^{32}$P]-labelled, bromodeoxyuridine-substituted DNA containing the minimal replication origin (i.e. no E2 binding sites). The DNA was subsequently digested and the proteins were analyzed by acrylamide gel electrophoresis. For E1 protein concentration: lanes A and C, 280 ng; Lanes B and D, 90 ng. For E2 concentration: lanes C–E, 100 ng.

DETAILED DESCRIPTION OF THE INVENTION

Figure 1A:
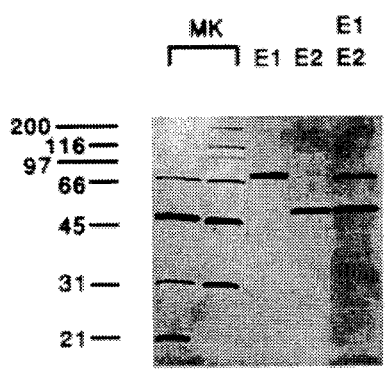
FIGS. 1A–C, BPV DNA replication in vitro. A, Purification of proteins. The BPV E1 and E2 coding sequences were cloned into a baculovirus expression system and the proteins were purified by immunoaffinity chromatography as described by Mohr et al.[13]. E1 was tagged at its amino-terminus with a 9 amino acids peptide (EE epitope) and purified with a monoclonal antibody specific to the tag pepfide (the antibody EE[20] was crosslinked to protein G Sepharose, Pharmacia LKB). After washing the loaded column with LiCI, the protein was eluted with 20 mM triethyl amine and concentrated (where necessary) by dialysis against solid polyethylene glycol (M.W. 8000), folllowed by extensive dialysis against 20 mM potassium phosphate (pH 7.5), 100 mM potassium glutamate, 1 mM EDTA, 1 mM DTT and 10% glycerol. In each lane 200 ng of the protein preparation was fractionated by SDS-PAGE and the proteins were stained with silver. The E2 and E1-E2 complex (designated E1/E2) were similarly purified with the monoclonal antibody specific to E2 (B202)[13]. MK, molecular weight markers (kilodalton). B, E1/E2 and BPV origin sequence-dependent in vitro DNA replication. In lanes labelled E1/E2+, 400 ngs of the purified E1/E2 complex were added. Three template DNAs are shown here: pKSO, contains BPV sequences from 7805-100; p3M contains the BPV-1 restriction fragment Hind III (6958)-Mlu (7351); and pKS is the vector plasmid (from Stratagene). I and II, form I and form II DNA; R.I., replicating intermediates. Both E1 with EE epitope at its N-terminus and the wild type E1 showed identical activities in ATPase and replication assay. However, E1 with EE epitope at its C-terminus was inactive in either assay (data not shown). C, Replicated form I DNA is resistant to Dpn I digestion. The replication products and 200 ngs of marker pKSO were mixed and separated by electrophoresis through a 1% SeaPlaque gel in 20 mM Tris-acetate (pH 8.0) buffer. The form I band was excised from the gel and hydrolyzed with Dpn I. Ethidium bromide staining showed that all detectable form I DNA was cleaved by the enzyme. MK, the pKSO replication products serve as a marker.

The invention described herein draws on previously published work and pending patent applications. By way of example, such work consists of scientific papers, patents or pending patent applications. All of these publications and applications, cited previously or below are hereby incorporated by reference.

The following methods were utilized to realize the use of the invention. Additional materials and methods are described in co-owned U.S. Ser. No. 632,027, filed Dec. 21, 1990.

The conditions for BPV replication in vitro were derived from Li and Kelly[21] with some modifications. Extracts from the mouse FM3A cell line were prepared as follows: Cells were grown in a 2-liter suspension culture containing RPMI 1640 media (supplemented with 25 mM HEPES, pH 7.2 and 5% calf serum). The cells were harvested at a density of $7 \times 10^5$ cells/ml. The cell pellet was washed with 30 mls of cold PBS and then 10 mls of hypotonic buffer (20 mM Hepes (pH 7.5), 5 mM KCl, 1 mM EDTA, 0.5 mM DTT). The cells were then resuspended in hypotonic buffer to a final volume of 10 mls and incubated on ice for 15 min. After 20 strokes in a Dounce homogenizer (with B pestol), 500 μl of 5M NaCl was added and the extraction mixture was incubated on ice for 30–60 min. This mixture was centrifuged in an SW41 rotor at 20K rpm for 30 min and the supernatant was dialyzed twice against 1 liter D buffer (20 mM HEPES, pH 7.5; 10 mM NaCl; 1 mM EDTA and 0.5 mM DTT). The extract was then centrifuge in HB4 rotor at 8K rpm for 8 min and the supernatant was frozen as droplets into liquid nitrogen. The protein concentration of the extract was typically 15–20 mg/ml and the frozen extract are kept at −71° C. and was good for at least one year. A standard replication assay (25 μl) contains: 10 μl extract, 40–80 ng of pure form I template DNA, 30 mM HEPES (pH 7.5), 7 mM MgCl$_2$, 20 mM potassium glutamate, 4 mM ATP, 100 μM each of CTP, UTP and GTP, 26 μM each of dATP, dTTP, dGTP and dCTP, 2.5 μCi each of the [$^{32}$P]-dNTP's, 40 mM phosphocreatine and 100 μg/ml creatine phosphokinase and viral proteins as indicated. The reaction was incubated at 37° C. for 2 hours, stopped by the addition of 25 μl of 20 mM Tris (pH 7.7), 20 mM EDTA, 2% SDS and 50 μg/ml proteinase K and incubated for another 30 min. The DNA was precipitated with 25 μl of 7.5M ammonium acetate and 175 μl of 95% ethanol. The precipitation was repeated twice and the DNA was resuspended in 50 µl TE. The DNA was analyzed by electrophoresis in 0.8% agarose gel. Dried gels were exposed to X-ray film. Extracts from FM3A cells are capable of efficient repair synthesis. This activity can be measured with damaged DNA templates, is independent of viral encoded proteins, and is essentially completed by 15 min of incubation (data not shown).

The experimental protocol for UV-crosslinking was carried out as previously described[22]. A primer annealed to the single-stranded pKSOM was extended by Klenow DNA polymerase in the presence of dCTP, dGTP, [a-$^{32}$P]dATP and 5-bromo-2'-deoxyuridine triphosphate. The double-stranded DNA was digested with restriction enzymes Bam HI and Eco RI, and the DNA fragment containing the minimal replication origin was isolated and used in the crosslinking reaction. E1 and E2 proteins were incubated with the labelled DNA at 37° C. for 30 min in 30 mM HEPES (pH 7.5), 7 mM MgCl$_2$, and 100 mM potassium glutamate. The reaction mixtures were then irradiated by UV for 60 min at room temperature. After digestion with DNase I and micrococcal nuclease, the E1, E2 proteins were separated in a 12% acrylamide gel by electrophoresis and detected by autoradiography.

Replication In Vitro is Dependent Upon Viral Proteins

Figure 1B:
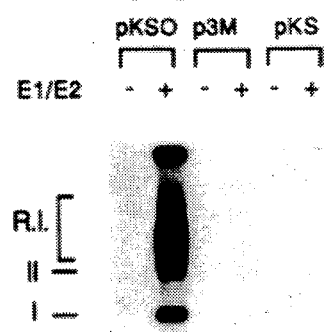

Cell-free extracts from viraly transformed cells (ID13) did not support the in vitro replication of exogenously added BPV-1 DNA (not shown). It seemed possible that virus-encoded proteins might be limiting. Therefore, E1, E2, and E1/E2 complex were overexpressed in a baculovirus expression system and the proteins purified by immunoaffinity chromatography as previously described[13] (FIG. 1A). When the purified E1/E2 complex was added to cell-free extracts from mouse ID 13 or FM3A cells[14], replication activity was observed. FIG. 1B shows that the replication products of pKSO plasmid co-migrated with supercoiled (I) and nicked (II) pKSO markers only when the FM3A extracts were supplemented with the E1/E2 complex. In addition, a broad band of replication intermediates (R.I) and high molecular weight forms were seen.

Figure 1C:
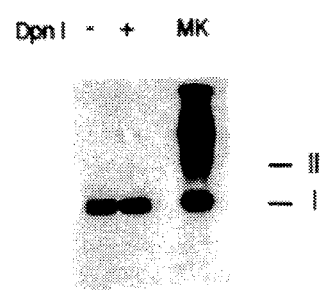

Initially plasmids containing the upstream regulatory region (URR)—previously shown to contain the origin of replication[15]—were used as templates for replication. Pure form I DNA template was used in these reactions to minimize repair synthesis. It was observed that completely replicated form I DNA increased with smaller template targets, thus smaller templates provide favorable substrates. Neither plasmid containing the late region of BPV-1 DNA (p3M) nor the vector (pKS) directed DNA replication (FIG. 1B). A number of experiments suggest that the heterogeneous material labeled R.I. in FIG. 1B are replication intermediates. For example, the heterogeneous material digested with single-cut restriction enzymes migrated more slowly than did open circle DNA. Also upon double digestion with single-cut enzymes and Dpn I (which cuts unreplicated DNA) the heterogeneous products migrated faster than the full-length linear DNA but slower than the largest Dpn-I fragment (dam not shown). Furthermore, the time course presented in FIG. 2 is consistent with a precursor—product relationship between the R.I. and the forms I and II DNA. Finally, FIG. 1C shows that the replicated DNA migrating with the mobility of supercoiled plasmid is completely resistant to hydrolysis by Dpn-1.

Table 1 summarizes some of the essential requirements and characteristics of the in vitro papilloma virus replication system. The aphidicolin inhibition suggests that one or more of the cellular DNA polymerases α, or δε[16] are involved in BPV-1 replication. Furthermore, the α-amanitin resistance implies that transcription per se mediated by the E2 protein and RNA polymerase II are irrelevant. The block to in vitro replication by topoisomerases (types I and II) inhibitors suggests that the reaction requires unwinding of the DNA duplex.

Figure 2A:
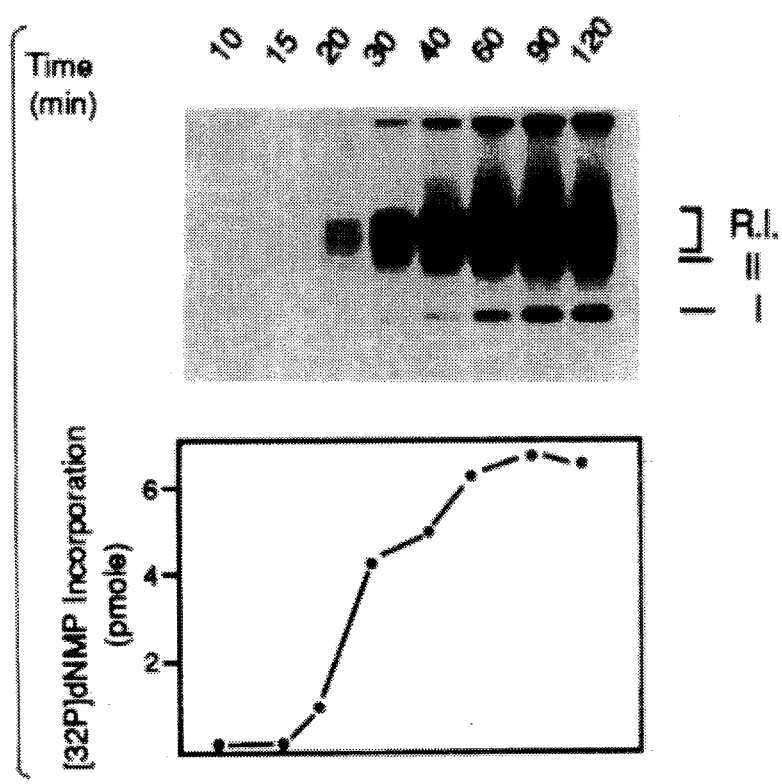
FIGS. 2A and 2B, BPV DNA replication in vitro initiates at an ori-containing fragment and proceeds bidirectionally. A, Time course of BPV DNA replication in vitro. The replication assay was scaled up to 200 μl. The reaction contained 640 ngs of pKSO, 2.2 μgs of E1 and 0.6 μgs of E2. At each indicated time point, 25 μl of reaction sample was taken and stoped. Top: an autoradiograph of the time course samples after electrophoresis. I and II, forms I and II of DNA. RI. replicating intermediates. Bottom: total incorporation into DNA of dNMP at each time point. B, Evidence for bidirectional replication. DNA samples from different time points were digested with Dra I and BstXI, and the resulting 7 DNA fragments (A–F) were separated in a 5% polyacrylamide gel. The autoradiogram of the gel is shown on the right. The intensity of each band was quantitated by the use of a Phosphor Imager (Molecular Dynamics). Incorporation per nucleotide was calculated for each fragment at each time point and the relative amounts of radioactivity were plotted (left side). Open circle: 20 min; Filled circle: 40 min; open square: 120 min. A diagram of the plasmid pKSO is shown at the bottom. Open arrow heads: Dra I sites. Filled arrow heads: Bst XI sites.
Figure 2B:
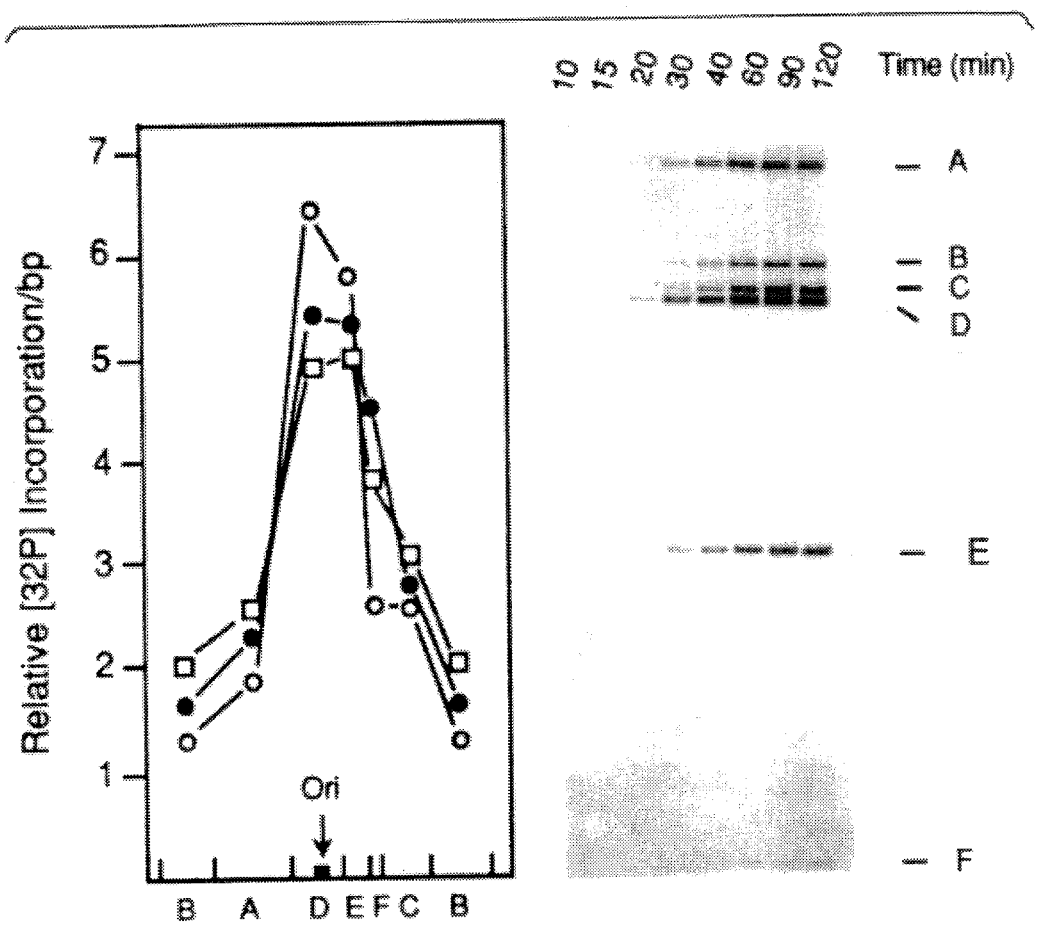

The kinetics of incorporation shown in FIG. 2A are consistent with a multicomponent or multistep reaction. After a lag period of approximately 15–20 minutes, the rate of synthesis increases for about 1 hour before reaching a plateau. At the plateau about 7 picomoles of dNTPs were synthesized into DNA in a 25 µl reaction. Similar reaction kinetics have been reported for the SV40 in vitro replication system[5,17,18]. To determine the initiation site and the directionality of DNA replication, the products from various time points were analyzed after digestion with Dra I and Bst XI. If replication initiates from within the BPV-1 sequences, fragment D should be labeled first. Subsequently, ff replication proceed bidirectionally, other fragments should become labeled in proportion to their molecular weight and position with respect to a unique start site. As shown in FIG. 2B, a symmetrical curve peaking at fragment D is observed. The curves do not completely flatten out with time, as replication intermediates predominate in the reaction, even after 2 hours of incubation (FIG. 2A).

The Minimal Origin of Replication

Figure 3:
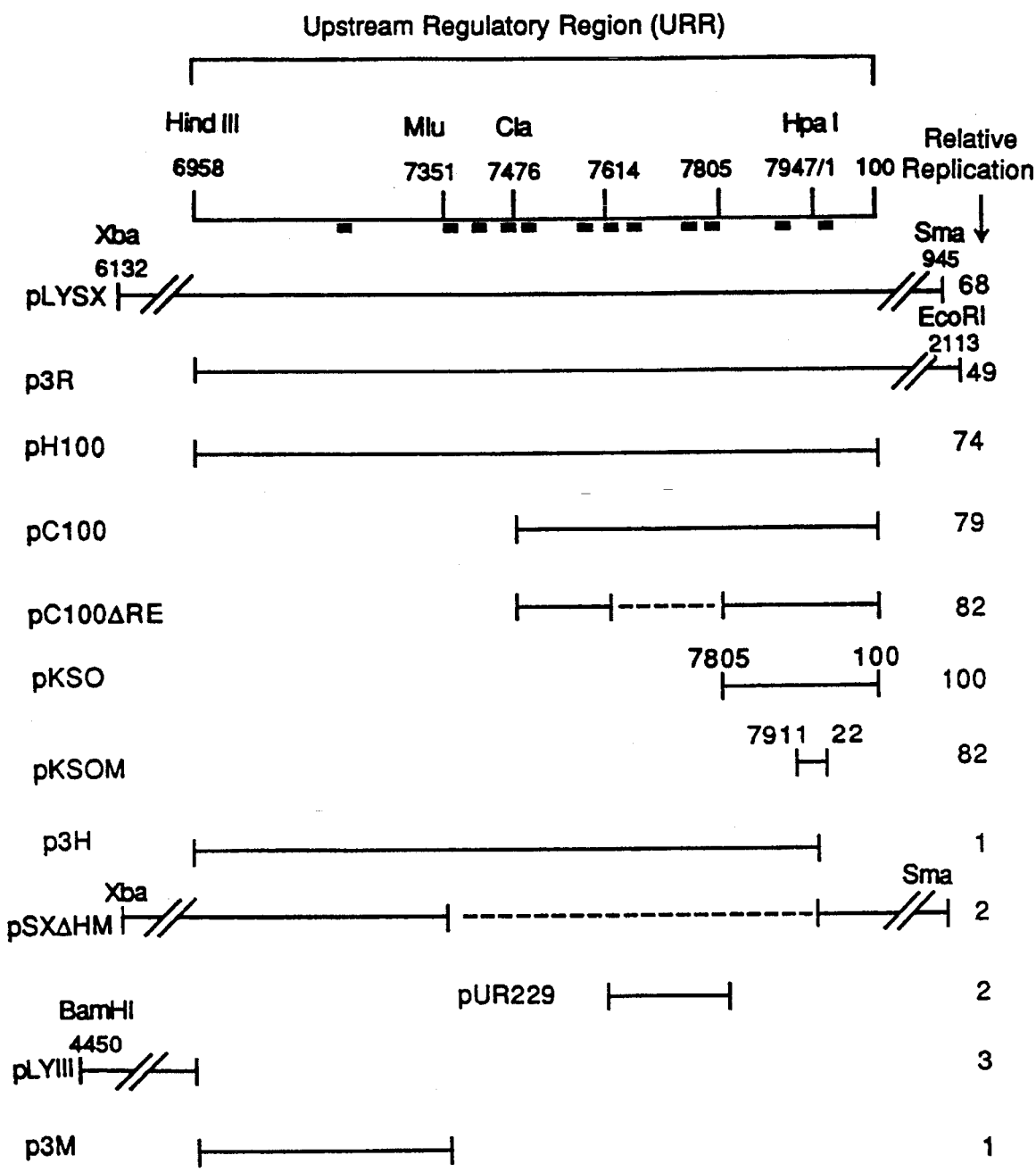
FIG. 3, Deletion analysis identifies cis elements required for replication. The physical map at the top shows the BPV URR which contains 12 E2 binding sites depicted as black boxes. DNA fragments spanning different regions of the viral genome were tested for their ability to function as an origin of DNA replication in the in vitro system. All reactions were carried out as described in FIG. 1 with 50 ng of DNA for each reaction. The quantitation was achieved by two protocols: direct counting of the incorporated label; and by scanning and integrating each gel lane for each sample. Six picomoles of net synthesis were obtained with pKSO, and this number was set as 100%. No discrete bands were detected for templates p3H through p3M (for example FIG. 1B), and these templates are judged to be completely negative for in vitro DNA replication. pKSOM spans nucleotides 7805-22 (59 bps) and is the smallest fragment tested to date which shows replication activity. Where coordinate numbers are given, PCR was used to create the BPV insert placed into the plasmid poly linker. All other fragments were inserted into the polylinker of the vector by restriction site fusions. For both pKSO and pKSOM, a Bam HI site was generated at the 5'-end and an Eco RI site at the 3'-end by PCR with primers.
Figure 4A:
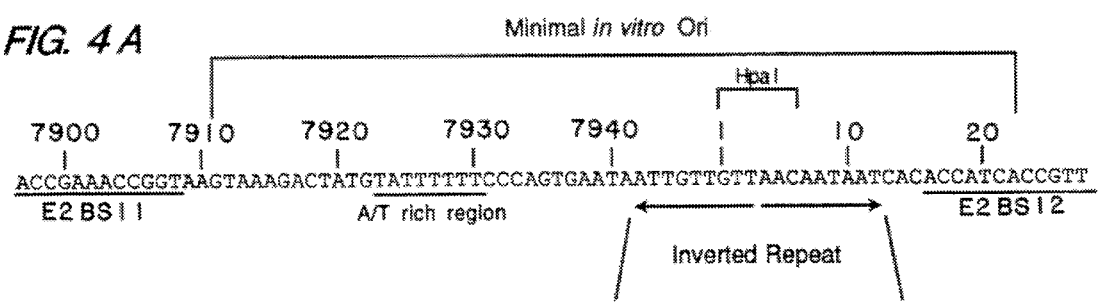
FIGS. 4A and 4B, Structure of the in vitro origin of BPV DNA replication. A, The top line shows the BPV sequence from E2 binding site 11 to E2 binding site 12. An 18 bp inverted repeat centered at the Hpa I site is indicated by two tail-to-tail arrows. An extensive homology between this inverted repeat and sequences present in the regulatory regions of the deer, elk, and human papilloma viruses is noted. B, Linker insertion at the center of the inverted repeat abolishes replication in vitro. An Nco I linker (CATGC-CATGGCATG) was inserted at the Hpa I site of pKSO and pKSOM. Standard replication assays were run on wild type and mutant templates. The lanes labelled "E1/E2+" contained 400 ng of the E1/E2 complex. All reactions were incubated at 37° C. for 2 hours.
Figure 4B:
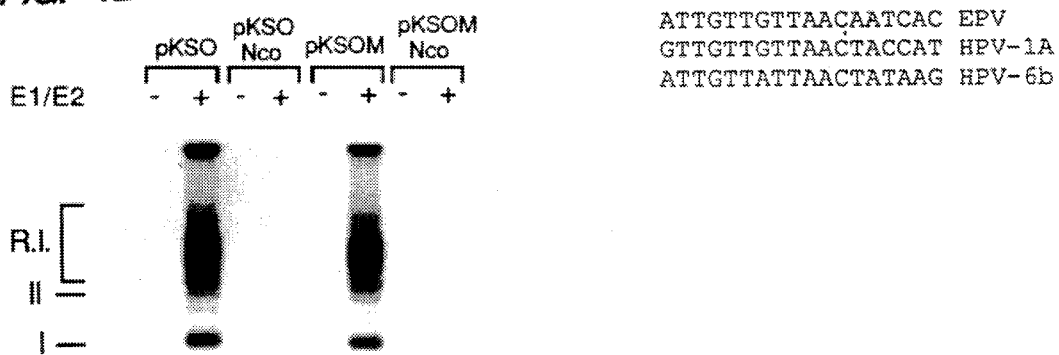

The series of plasmids used to localize the genetic elements necessary for BPV in vitro DNA replication are shown in FIG. 3. We were surprised to find that plasmid PC100ΔRE replicated with the same efficiency as did the intact URR (FIG. 3), as this plasmid does not contain the highest affinity binding sites for the E1/E2 complex[3]. However, at higher concentrations the complex bound to other regions of the URR. In the absence of E2, E1 displayed a weak affinity for DNA proximal to but outside of these high affinity sites (see FIG. 3, Mohr et. al.B). Consistent with our data, In vivo studies of BPV-1 replication supported the notion that these high affinity sites are unnecessary in cis as genetic elements for replication[9]. Of the plasmids that replicated in vitro, pKSOM contains the least amounts of vital DNA. This plasmid contains a part of E2 binding site 12 [12], an A/T rich region and an 18 base pair palindromic sequence (FIGS. 3 and 4). This palindromic sequence motif is conserved in a number of animal and human papilloma viruses. To examine the genetic significance of this palindromic sequence, mutants were created by inserting a synthetic linker into the Hpa-I site (FIG. 4A). Neither pKSO-Nco nor pKSOM-Nco were capable of supporting in vitro replication (FIG. 4B). These restfits suggest that the spacing between palindrpmic half sites are important for replication in vitro.

E2 Stimulates DNA Replication

Figure 5A:
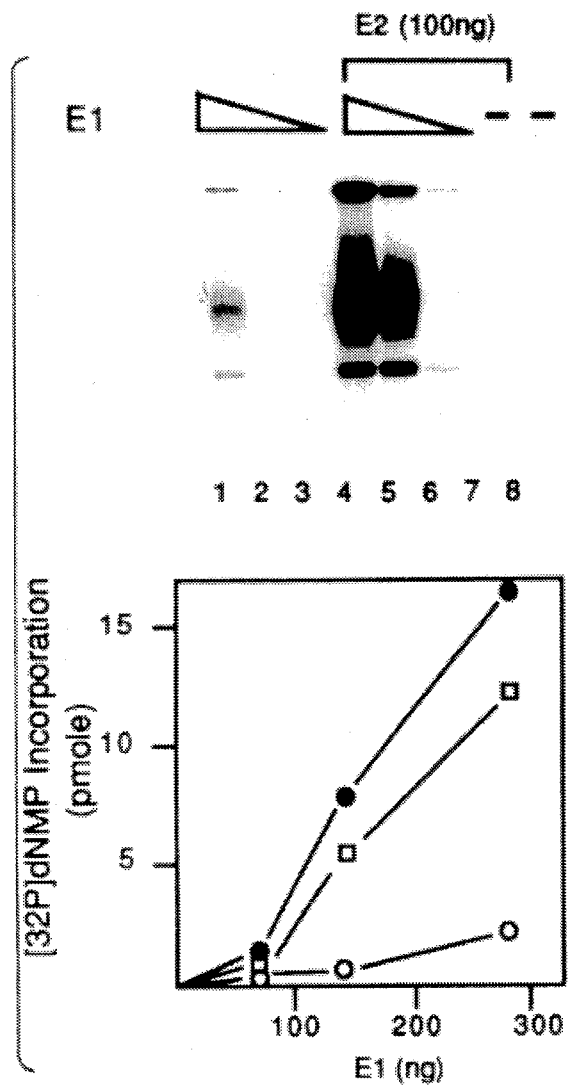
FIGS. 5A and 5B, E2 stimulates E1 dependent replication. A, pKSO which contains both E2 binding site 11 and 12 was used as the template DNA. Standard replication assays were performed either in the presence or absence of E1, E2 proteins at 37° C. for 2 hours. Top, an autoradiogram of the replication products after fractionation by gel electrophoresis. The amounts of the viral proteins in each reaction is: E1: 280 ng (lanes 1 and 4); 140 ng (lanes 2 and 5); 70 ng (lanes 3 and 6). E2:100 ng (lanes 4–7). No added protein control: lane 8. Bottom, a set of E1 and E2 titration experiments were carried out and the [$^{32}$P] incorporation was quantitated and plotted as shown. B, pKSOM which contains no E2 binding site was used as the template DNA. Top, autoradiogram of the replication products. E1: 280 ng (lanes 11 and 14); 140 ng (lanes 12 and 15); 70 ng (lanes 13 and 16). E2: 100 ng (lanes 14–17). No added protein control: lane 18. Bottom, The fitration of E1 and E2 protein concentrations and replication for the pKSOM template. Symbols for this figure: open circles, no E2; filled circles, 100 ng of E2; open square, 30 ng of E2. E2 concentration above 100 ng gave no further stimulation (not shown).
Figure 5B:
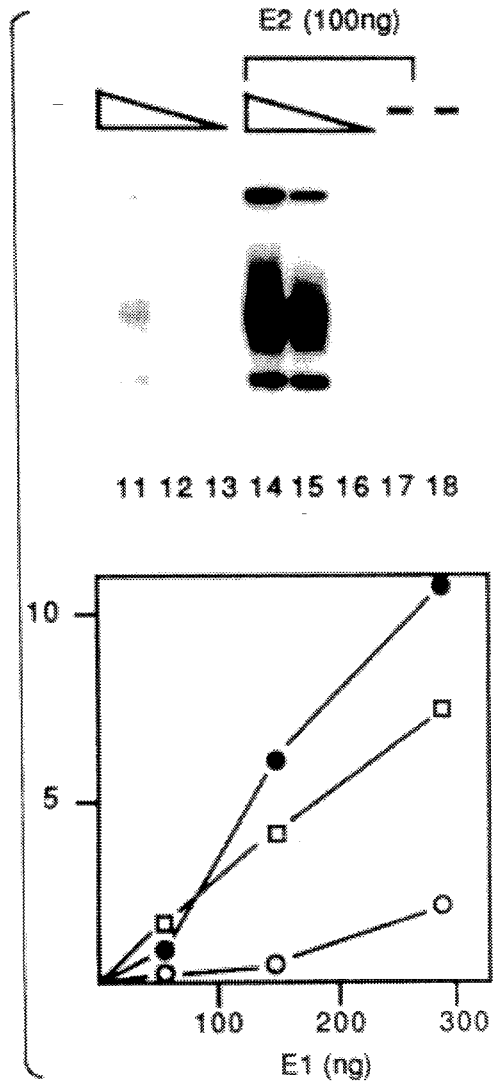

The in vitro replication system for BPV-1 was employed to examine the role E2 plays in DNA synthesis. Reactions receiving only E2 protein failed to replicate BPV-1 templates (FIG. 5 lanes 7 and 17). Reactions supplemented with only purified E1 protein directed a small amount of replication only at the highest levels of E1 (FIG. 5 lanes 1 and 11). When the purified E2 protein was added to extracts along with the purified E1 protein, a marked stimulation of replication was observed (FIG. 5 top and bottom panels). Similar incorporation was detected utilizing two different templates pKSO or pKSOM. The stimulation was due specifically to the E2 protein[19], as the E2C. protein[19], purified in a manner identical to E2, did not activate E1. As shown in FIG. 5, the extent of E2 stimulation was dependent upon the concentration of both E2 and E1. Significantly, at low E1 concentrations, replication was absolutely dependent upon E2. The absolute levels of the E1 protein in vivo during S phase are not known, but we suspect that it is lower than that of the E2 protein which we estimate to be about a few thousands molecules per cell. The absolute requirement for the E2 protein in vivo may thus reflect at least in part the low levels of the E1 protein in vivo.

To determine if interactions between E1 and E2 might mediate cooperative DNA binding, DNase footprinting studies were initiated. FIG. 6A & B shows a DNase footprint analysis of purified E1 protein in the presence and absence of purified E2. E1 alone clearly protects DNA sequences centered over the 18 b.p. palindrome (labeled Ori) of pKSO. The linker insertion mutation pKSO-Nco dramatically diminishes this protection (data not shown). The E2 protein does indeed enhance the DNA binding ability of the E1 protein. Protection of the E1 binding site in the presence of E1 and E2 occurs at 10 fold lower E1 concentrations than those which generate equivalent amounts of protection in the absence of E2. Surprisingly, cooperativity was also seen with templates pKSOM lacking intact E2 binding sites. The UV crosslinking experiment shown in FIG. 6C extends this point. E2 could not be crosslinked to the DNA in the absence of E1, because no E2 sites exist in this target. However, in the presence of the E1 protein the E2 protein can be crosslinked to the DNA (FIG. 6C, lanes C,D). Together with the footprint analysis provided above, it is clear that the E1 and E2 proteins help stabilize the formation of a complex containing both proteins over the replication origin.

Table 1

The "complete" system is the standard reaction mixture described in FIG. 1 and set as 100% for relative replication comparisons. The [$^{32}$P] incorporation was quantitated by scintillation counting in EcoLite (ICN Biochemicals). The actual counts incorporated for the complete reaction was 40,000 cpm (9.4 pmol). The counts for the reaction containing no template DNA was 1,000 (0.2 pmol) and set to 0%. DNA topoisomerase I inhibitor camptothecin and topoisomerase II inhibitor V-M-26 were gifts from Prof. L. F. Liu (Johns Hopkins School of Medicine).

| Requirement for BPV DNA Replication In Vitro | |
| --- | --- |
| Conditions | Relative Replication |
| Complete | 100 |
| −Template DNA | 0 |
| −ATP | 18 |
| −CTP, UTP and GTP | 71 |
| −Phosphocreatine and Creatine phosphokinase | 22 |
| +Aphidicolin 10 µg/ml | 0 |
| 30 µg/ml | 0 |
| +α-Amanitin 100 µg/ml | 99 |
| 250 µg/ml | 81 |
| +Camptothecin and VM-26 (40 µg/ml of each) | 3 |

REFERENCES

1. Mohr, I. J., Stillman, B. & Gluzman, Y. *EMBO J.* 6, 153–160 (1987).
2. McVey, D., et al. *Nature* (London) 341, 503–507 (1989).
3. D'Urso, G., Marraeeino, R. L., Marshak, D. R. & Roberts, J. M. *Science* 250, 786–791 (1990).
4. Din, S. U., Brill, S. J., Fairman, M. P. & Stillman. *Genes & Dev.* 4, 968–977 (1990).
5. Virshup, D. M., Kauffman, M. G. & Kelly, T. J. *EMBO J.* 8, 3891–3818 (1989).
6. Depamphilis, M. L. *Cell* 52, 635 (1988).
7. Brand, A. H., Micklem, G. & Nasmyth, K. *Cell* 51,709 (1987).
8. Hatton, K. S., et al. *Cancer Cell* 6, 335–340 (1988).
9. Ustav, M. & Stenlund, A. *EMBO J.* 10, 449–457 (1991).
10. Sun, S., Thorner, L., Lentz, M., MacPherson, P. & Botchan, M. *J. Virol.* 64, 5093–5105 (1990).
11. Howley, P. M. in Virology (eds. Fields, B. N. & Knipe, D. M.) 1625–1650 (Raven Press, N.Y., 1990).
12. Li, R., Knight, J. D., Jackson, S. P., Tjian, R. & Botchan, M. R. *Cell* 65, 380–400 (1991).
13. Mohr, I. J., et al. *Science* 250, 1694–1699 (1990).
14. Nakano, N. *J. Exp. Med.* 88, 69–84 (1966).
15. Yang, L. & Botchan, M. *Mol. Cell Biol.* 64, 5903–5911 (1990).
16. Syväoja, J., et al. *Proc. Nat. Acad. Sci. USA* 87, 6664–6668 (1990).
17. Stillman, B. & Gluman, Y. *Mol. Cell Biol.* 5, 2051–2060 (1985).
18. Wobbe, C. R., Dean, F. B., Murakami, Y., Weissbach, L. & Hurwitz, J. *Proc. Natl. Acad. Sci. USA* 83, 4612–4646 (1986).
19. Knight, J., Li, R. & Botchan, M. *Proc. Natl. Acad. Sci. USA* 88, 3204–3208 (1991). Grussenmeyer, T., Scheldtmann, K., Hutchinson, M. A., Eckhart, W. & Walter, G. *Proc. Natl. Acad. Sci. USA* 82, 7952–7954 (1985).
21. Li, J. J. & Kelley, T. J. *Proc. Natl. Acad. Sci. USA* 81, 6973–6977 (1984).
22. Lin, S. Y. & Riggs, A. D. *Proc. Natl. Acad. Sci. USA* 71, 947–951 (1974).

The present invention has been described with reference to specific embodiments. However, this application is intended to cover those changes and substitutions which may be made by those skilled in the art without departing from the spirit and the scope of the appended claims.

We claim:

1. A composition for replicating papilloma virus DNA, comprising papilloma virus proteins E1 and E2, and a cell free extract that causes papilloma virus DNA replication.

2. A cell-free composition for replicating papilloma virus DNA, comprising papilloma virus proteins E1 and E2, cellular DNA polymerases, and topoisomerases.

3. A composition for replicating papilloma virus DNA, comprising papilloma virus protein E1 and a cell free extract that causes papilloma virus DNA replication, wherein the concentration of protein E1 is elevated such that papilloma virus DNA replication occurs in the absence of protein E2.

4. A method of identifying a compound that inhibits papilloma virus DNA replication, comprising the steps of:

a) isolating a cell free extract that causes papilloma virus DNA replication in the presence of papilloma virus proteins E1 and E2;

b) forming a mixture comprising said cell free extract, E1 and E2, assay reagents that support and permit the determination of papilloma virus DNA replication, and said compound; and c) measuring the amount of DNA replication that occurs in the presence of said compound compared to the amount that occurs in its absence.

5. A method as described in claim 4, wherein said cell free extract also causes papilloma virus DNA replication in the absence of E2 and in the presence of an elevated concentration of E1.

6. A method as described in claim 4, wherein said cell free extract is replaced with cellular DNA polymerases and topoisomerases.

7. A method of identifying a compound that inhibits papilloma virus DNA replication, comprising the steps of:

(a) isolating a cell free extract that causes papilloma virus DNA replication in the presence of an elevated concentration of papilloma virus protein E1;

(b) forming a mixture comprising said cell free extract and E1 protein, assay reagents that support and permit the determination of papilloma virus DNA replication, and said compound; and (c) measuring the amount of DNA replication that occurs in the presence of said compound compared to the amount that occurs in its absence.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CATGCCATGG CATG 14

( 2 ) INFORMATION FOR SEQ ID NO:2:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

ACCGAAACCG GTAAGTAAAG ACTATGTATT TTTTCCAGT GAATANBBRB BRBBNNCNNB 60

NNBCACACCA TCACCGTT 78